(12) United States Patent
Stadelhofer

(10) Patent No.: US 8,567,390 B2
(45) Date of Patent: Oct. 29, 2013

(54) DISCHARGE DEVICE FOR NASAL APPLICATION

(75) Inventor: Peter Stadelhofer, Singen (DE)

(73) Assignee: Aptar Radolfzell GmbH, Radolfzell (DE)

(*) Notice: Subject to any disclaimer, the term of this patent is extended or adjusted under 35 U.S.C. 154(b) by 891 days.

(21) Appl. No.: 12/316,231

(22) Filed: Dec. 10, 2008

(65) Prior Publication Data

US 2009/0159081 A1   Jun. 25, 2009

(30) Foreign Application Priority Data

Dec. 20, 2007   (DE) .................. 10 2007 063 213

(51) Int. Cl.
*A61M 11/00* (2006.01)

(52) U.S. Cl.
USPC ............. 128/200.22; 128/200.14; 128/200.21

(58) Field of Classification Search
USPC ............. 128/200.23, 203.15, 203.12, 203.18, 128/200.14, 200.21, 200.22; 222/255, 256, 222/321.9, 491, 493, 496
See application file for complete search history.

(56) References Cited

U.S. PATENT DOCUMENTS

| | | | |
|---|---|---|---|
| 2,195,554 A | | 4/1940 | Beardsley |
| 3,666,182 A | * | 5/1972 | Cureton .................. 239/327 |
| 3,809,084 A | * | 5/1974 | Hansen ................ 128/203.15 |
| 3,812,853 A | * | 5/1974 | Crain .................. 128/200.17 |
| 5,702,362 A | * | 12/1997 | Herold et al. .................. 604/58 |
| 6,427,680 B1 | | 8/2002 | Oechsel |
| 6,745,760 B2 | * | 6/2004 | Grychowski et al. ..... 128/200.14 |
| 2002/0017294 A1 | * | 2/2002 | Py ........................ 128/200.23 |
| 2003/0180351 A1 | * | 9/2003 | Gluck et al. .................. 424/450 |
| 2006/0084908 A1 | * | 4/2006 | Bonney et al. .................. 604/19 |
| 2006/0118107 A1 | * | 6/2006 | King ........................ 128/200.23 |
| 2006/0137683 A1 | | 6/2006 | Anderson et al. |
| 2006/0255071 A1 | * | 11/2006 | Behar et al. .................. 222/256 |
| 2008/0092881 A1 | | 4/2008 | Pearson et al. |

FOREIGN PATENT DOCUMENTS

| | | |
|---|---|---|
| DE | 40 37 783 A1 | 9/1991 |
| DE | 195 27 943 A1 | 2/1997 |
| FR | 517.936 | 5/1921 |
| FR | 2 764 807 | 12/1998 |
| WO | WO 01/78818 A2 | 10/2001 |
| WO | WO 2006/097753 A1 | 9/2006 |

OTHER PUBLICATIONS

Examination Report of European Patent Office dated Apr. 26, 2010 (6 pages).
European Patent Office Search Report dated Jun. 3, 2009 (7 pages).

* cited by examiner

*Primary Examiner* — Jackie Ho
*Assistant Examiner* — Peter S Vasat
(74) *Attorney, Agent, or Firm* — Flynn, Thiel, Boutell & Tanis, P.C.

(57) ABSTRACT

Discharge device for nasal application of medicaments.
The invention relates to a discharge device (10) for nasal application of medicaments, with a main body (A) having a contact surface (10*b*) which, during use, is vertically oriented and is directed toward the face of the user, and with a nosepiece (70) which is arranged in a fixed position with respect to the main body (A) and is designed to be inserted into a nostril of the user, which nosepiece (70) is provided on an upper edge area of the contact surface (10*b*), protrudes from the contact surface (10*b*) and has a discharge opening (72).
Use as a discharge device that counteracts incorrect use.

12 Claims, 3 Drawing Sheets

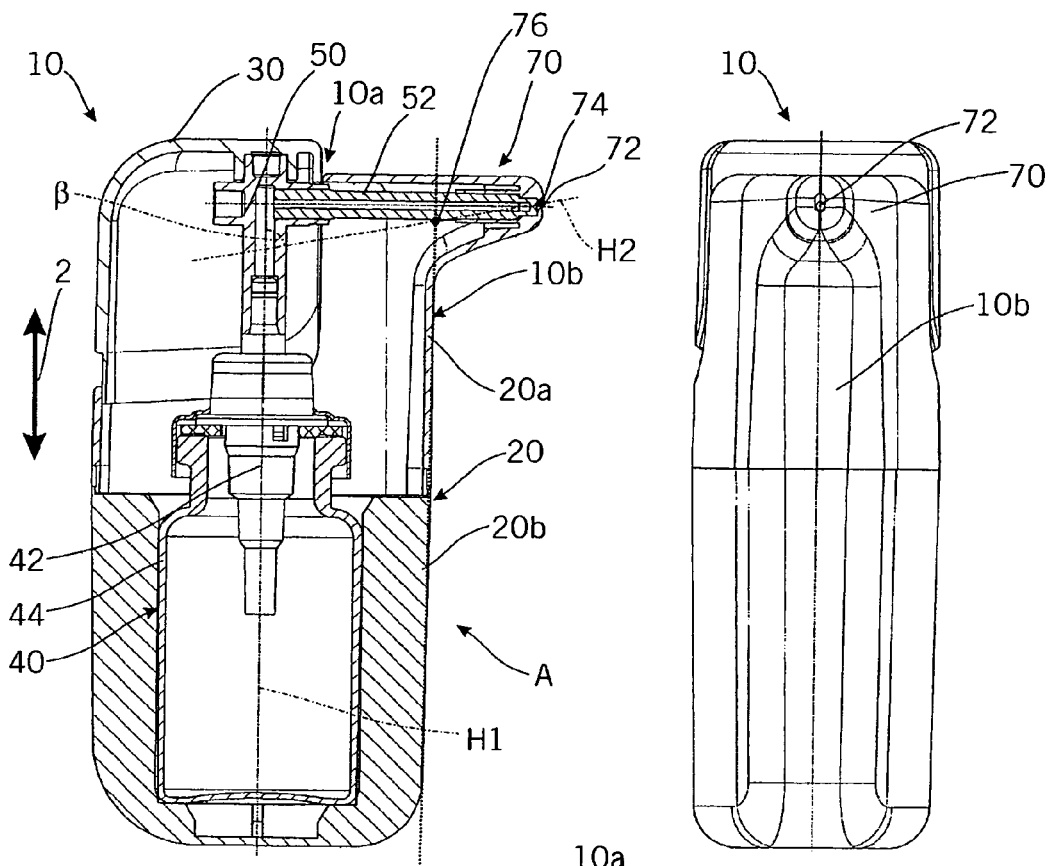
Fig. 1
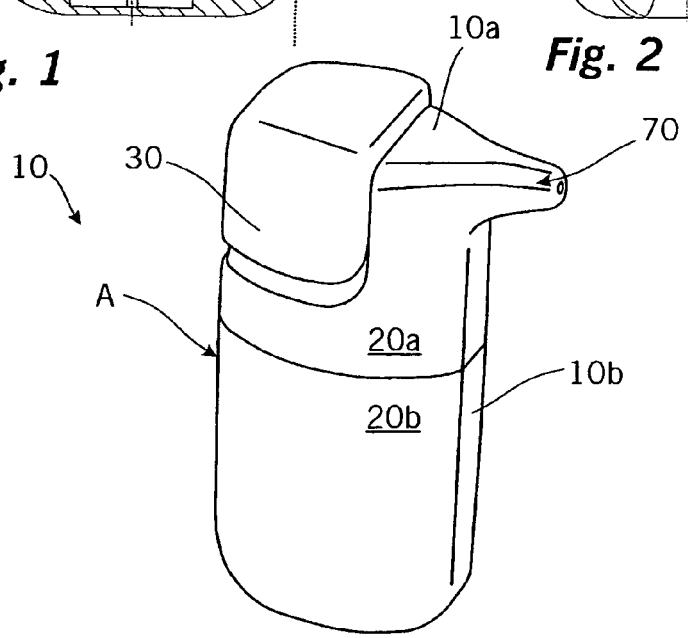
Fig. 2
Fig. 3

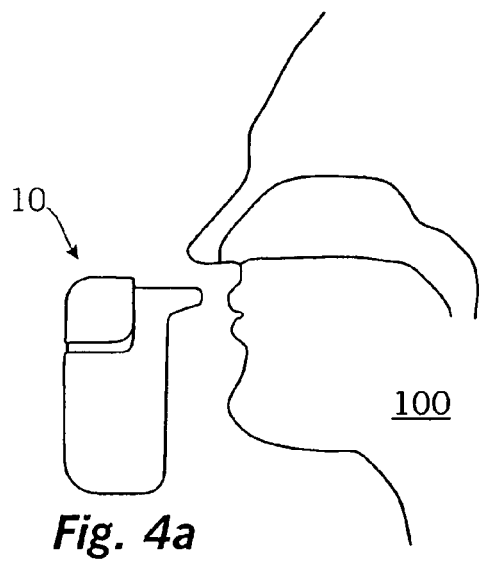
*Fig. 4a*
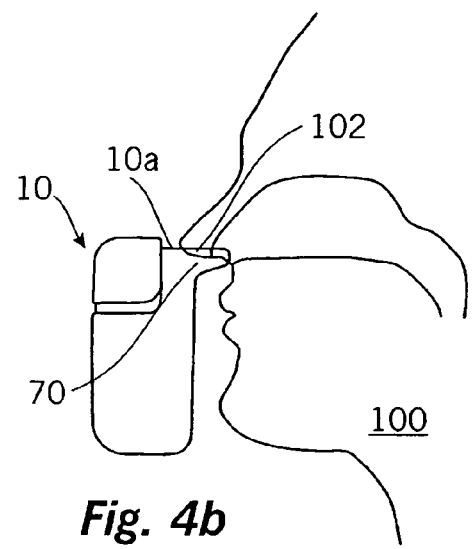
*Fig. 4b*
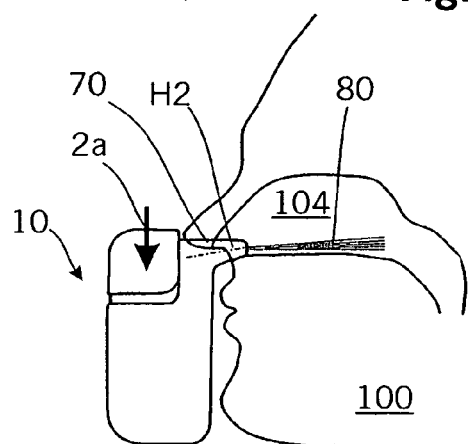
*Fig. 4c*
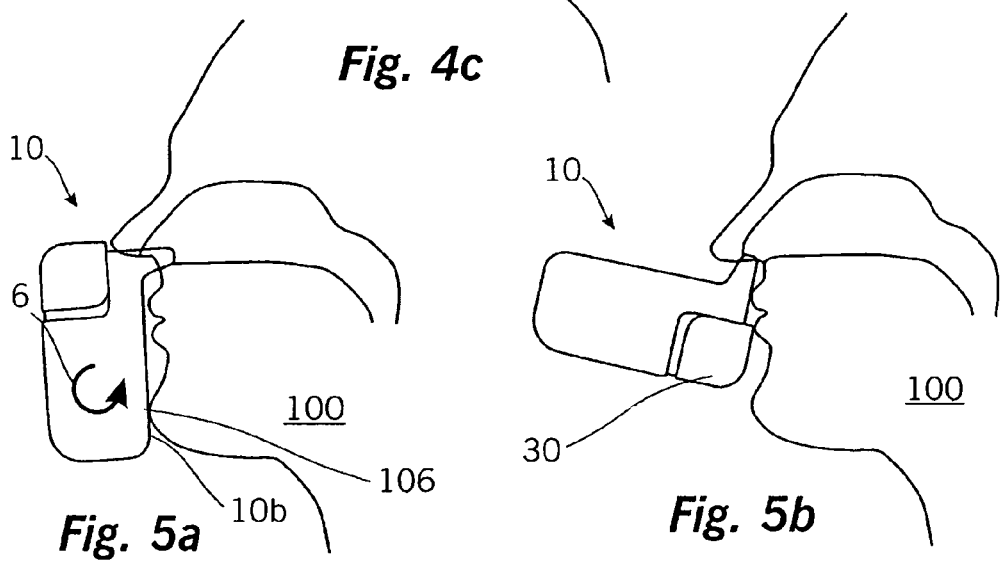
*Fig. 5a*
*Fig. 5b*

DISCHARGE DEVICE FOR NASAL APPLICATION

FIELD OF THE INVENTION AND PRIOR ART

The invention relates to a discharge device for nasal application of medicaments.

Discharge devices of this kind are mostly used in the form of nasal sprays that are intended to alleviate the symptoms of colds. A particularly common type of discharge device has a nosepiece that extends from a main body, in the principal direction of extent of the latter, and that is designed to discharge in the direction of this principal direction of extent. The disadvantage of this type of discharge device is that the intuitive application by the user in most cases means that the user holds the discharge device, and therefore the nosepiece, in such a way that the discharge takes place almost vertically. From the medical point of view, however, this is not ideal, because the nasal cavity to be reached is arranged behind the nostrils and not, as is commonly believed, above them. The almost horizontal direction of discharge, which is advantageous from the medical point of view, is in most cases not achieved by the described type of discharge device.

Although the prior art, for example DE 195 27 943 A1, also discloses spray bottles for ear drops in which a nozzle is pivotable relative to the principal direction of extent of the bottle storing the corresponding medium, these permit variable adjustment of the direction of pivoting, and this makes it very easy for a user to return to the customary and disadvantageous manner of discharging the spray in an almost vertical direction.

To ensure the correct direction of discharge, the US patent application US 2006/0137683 proposes that the discharge opening be arranged, on what is otherwise a mainly conventionally designed nosepiece, in such a way that the spray is not oriented in the principal direction of extent of the nosepiece but instead at an angle of approximately 90° to this. Accordingly, the nosepiece is inserted vertically into the nostril, in the manner adopted by most users, and then leads to a spray that is oriented approximately horizontally.

A disadvantage of this design, however, is that it is difficult for the user to estimate how far the nosepiece is to be inserted into the nostril before the medium can be sprayed. If the medium is discharged before the ideal position of the nosepiece is reached, it deposits in the nostril without reaching the nasal cavity.

OBJECT AND SOLUTION

The object of the invention is to make available a discharge device for nasal application of medicaments which is intuitively handled correctly by the user and which has spraying characteristics that are advantageous from the medical point of view.

According to the invention, this is achieved by a discharge device for nasal application that comprises a main body having a contact surface which, during use, is vertically oriented and is directed toward the face of the user, and that further comprises a nosepiece which is arranged in a fixed position with respect to the main body and is designed to be inserted into a nostril of the user, which nosepiece is provided on an upper edge area of the contact surface, protrudes from the contact surface and has a discharge opening.

In the context of this invention, observations concerning orientation and direction, for example "top", "and", "vertical" and "horizontal", relate to a situation of use in which the user, with his head upright, holds the discharge device in its correct orientation. A different position of the user, for example lying down, or a situation where the discharge device is not in use, for example in the state during storage, accordingly leads to a corresponding change in the observations made below concerning direction and orientation.

The discharge device according to the invention has a main body which preferably accommodates all the component parts needed for the storage and delivery of the medium, in particular a media reservoir, a delivery device or pump arrangement, and media lines that form a path for the medium from the media reservoir to the discharge opening. On one side, the discharge device has a contact surface whose purpose is to make the correct orientation of the discharge device intuitive to a user and to make a medically undesirable orientation impossible or difficult. During correct use, this contact surface is directed toward the lower half of the user's face and is located directly in front of the mouth and/or chin of the user or lies directly on these parts of the body. The nosepiece, which protrudes from this contact surface and in this way points toward the user in the described position, is pushed into a nostril of the user. The nosepiece, which is provided on an upper edge area of the contact surface, thus extends at least with a horizontal direction component into a nostril of the user. In a particular embodiment, two nosepieces are provided on the contact surface and allow the medium to be discharged simultaneously into both nostrils of the user.

The fixed position of the nosepiece relative to the main body results in particularly comfortable use, since the hand with which the user grips the main body can be easily held in a fixed position relative to the user's nose, and this in turn also leads to a fixed position of the nosepiece relative to the nose. Actuation of the discharge device does not cause the unpleasant sensation of the nosepiece shifting into the nose or out of the nose.

A disadvantageous orientation of the discharge device deviating from this one, particularly an orientation in which the nosepiece assumes an approximately vertical orientation, can be adopted only with difficulty when using the discharge device according to the invention, since this is prevented by the contact surface abutting against the mouth and/or chin. Although the discharge device could be pivoted in its entirety through 90° about the principal direction of extent of the nosepiece, the resulting asymmetrical position, in which the contact surface is provided either to the right or left of the nose, makes it immediately apparent to the user that this cannot be the correct position. The contact surface itself does not have to be completely flat, but is at the very most slightly curved in the vertical. The surface is preferably completely flat at least in some areas. It does not need to have any great width, since the important point is that it comes to bear on the mouth and/or chin of the user. A width of a few millimeters, preferably of 10 mm or slightly more, is considered preferable. The height of the contact surface is preferably at least 40 mm, in particular preferably at least 60 mm. This ensures secure contact on the mouth and if appropriate on the chin.

The nosepiece protrudes preferably by at least 10 mm from the contact surface. This distance relates to a distal end of the nosepiece and to a surface perpendicular to the contact surface or to an imaginary surface flush with the latter. The length of 10 mm ensures that the nosepiece engages securely in the nostril in the horizontal direction. Particular preference is given to embodiments with the nosepiece protruding by at least 15 mm, in particular by at least 20 mm.

In a preferred embodiment of the invention, the principal direction of extent of the main body is parallel to the vertically oriented contact surface. The principal direction of extent of the main body corresponds to the spatial direction in which the main body has the greatest extent. In a preferably approximately cylindrical configuration of the main body, the principal direction of extent corresponds to the cylinder axis. The principal direction of extent of the main body preferably runs substantially vertically or at an angle of less than 150 to the vertical. The main body in this way has a generally slender configuration which already suggests a vertical orientation of the main body during actuation. The slender configuration is also particularly of advantage in terms of handling.

A principal direction of extent of the nosepiece preferably encloses an angle of between 45° and 90°, particularly of between 60° and 90°, with the vertical. It is particularly advantageous if the principal direction of extent is almost at right angles to the vertical, i.e. horizontal. The principal direction of extent of the nosepiece is regarded as that direction in which the nosepiece is moved for insertion into the nostril. This principal direction of extent preferably corresponds to a direction parallel to an imaginary line that is defined by two points, on the one hand the distal end of the nosepiece and on the other hand the center point of the cross-sectional surface area of the nosepiece in the plane of the contact surface. This configuration ensures that the nosepiece can be inserted particularly easily into the nostril. Because of the large angle enclosed by the nosepiece with the vertical, the movement of insertion is close to a horizontal movement.

In a particularly preferred embodiment, the nosepiece is provided in a transition area between the contact surface and a top face of the main body.

It is particularly advantageous if the nosepiece merges flush into a top face of the main body. For this purpose, a continuous surface free of steps or edges is provided that extends from the top face of the main body to a top face of the nosepiece. In particular, the flush configuration advantageously allows the discharge device to be moved toward the nose from underneath until a wing of the nose is gently lifted by the nosepiece. The discharge device can then be brought substantially horizontally toward the user, in the process of which the nosepiece is introduced into the nostril associated with the wing of the nose, and the top face of the main body supports the wing of the nose in its lifted position.

The nosepiece can be designed in such a way that its principal direction of extent and the discharge direction differ from each other, for example deviating by as much as 90°. However, it is considered particularly advantageous if a principal direction of extent of the nosepiece encloses an angle of between 0° and 30° with a discharge direction defined by the geometry of the discharge opening. This angle is preferably 0°, such that the discharge direction coincides with the principal direction of extent of the nosepiece.

It is considered particularly advantageous if a discharge device of the type described has an actuating handle which is arranged on a top face of the main body and/or is movable relative to the main body in an actuating direction, said actuating direction enclosing, with a principal direction of extent of the nosepiece, an angle of between 75° and 90°.

The design with the actuating handle on the top face of the main body permits comfortable actuation with index finger or thumb. The actuating handle is preferably arranged in such a way that the actuation is not restricted by the nose itself. For this purpose, the actuating handle is preferably at least so arranged, or so dimensioned, that actuation is possible at a distance of approximately 20 mm from the contact surface which bears on the mouth, in the area of the upper lip, at the time of actuation. The actuating handle is preferably arranged on that side of the top face directed away from the contact surface. The arrangement on the top face of the main body has the advantage that incorrect orientation of the discharge device is made difficult. If a user holds the discharge device in such a way that the substantially horizontal nosepiece is oriented vertically on account of the discharge device having been turned through 180°, the actuating handle consequently lies in the area of his mouth or chin and cannot therefore be easily actuated. The incorrect holding of the discharge device is in this way made obvious to the user. The design of the actuating handle in which an actuating direction encloses an angle of 75° to 90° with the principal direction of extent of the nosepiece results in particularly comfortable actuation, since the actuation has no effect or only a minimal effect on the position of the nosepiece within the nose of the user. Since the force acting on the actuating handle and the corresponding force acting on the main body is almost orthogonal to the direction of insertion of the nosepiece, the force does not push the nosepiece further into the nose or withdraw it from the nose.

As regards the structure of the main body, it is considered particularly advantageous if a pump arrangement is provided whose pumping direction encloses an angle of between 0° and 10° with the vertical. In this way, an actuation of the actuating device approximately in the direction of the vertical can be used directly, without further means of deflection, to actuate the pump arrangement.

It is also considered particularly advantageous if the main body accommodates a separately handled pump dispenser which comprises a media reservoir and a pump arrangement. A separately handled pump dispenser of this kind is particularly inexpensive to produce and permits a particularly simple design of the other components of the discharge device, since the somewhat complex components of the discharge device such as the media reservoir and the pump arrangement are already provided in the separately handled pump dispenser. The pump arrangement of the pump dispenser is preferably connected to the discharge device via a flexible conduit such as a plastic tube.

In a development of the invention, the contact surface has a configuration whose shape is adapted to the shape of the lip area and/or chin area of a user. This makes it immediately obvious to the user how to correctly hold the discharge device. The configuration of the contact surface, and the protrusion of the nosepiece from this contact surface, can be such that the contact surface is designed to rest flat on the lips and/or chin of the user. However, in an embodiment of the discharge device in which the contact surface remains at a distance from the lips and/or chin, it is expedient to provide the contact surface in such a shape as to make the desired information on the correct holding of the discharge device obvious to the user.

BRIEF DESCRIPTION OF THE DRAWINGS

Other features and advantages of the invention will become evident from the claims and also from a description of two preferred illustrative embodiments of the invention which are explained below. In the drawing:

FIG. 1 and FIG. 2 show a discharge device according to the invention in a sectional side view and in a non-sectional front view, FIG. 3 shows the discharge device from FIGS. 1 and 2 in a perspective view, FIGS. 4a through 4c show the correct use of the discharge device from FIGS. 1 through 3, FIGS. 5a and 5b show incorrect uses of the discharge device from FIGS. 1 through 3.

DETAILED DESCRIPTION OF THE ILLUSTRATIVE EMBODIMENTS

Figure 6:
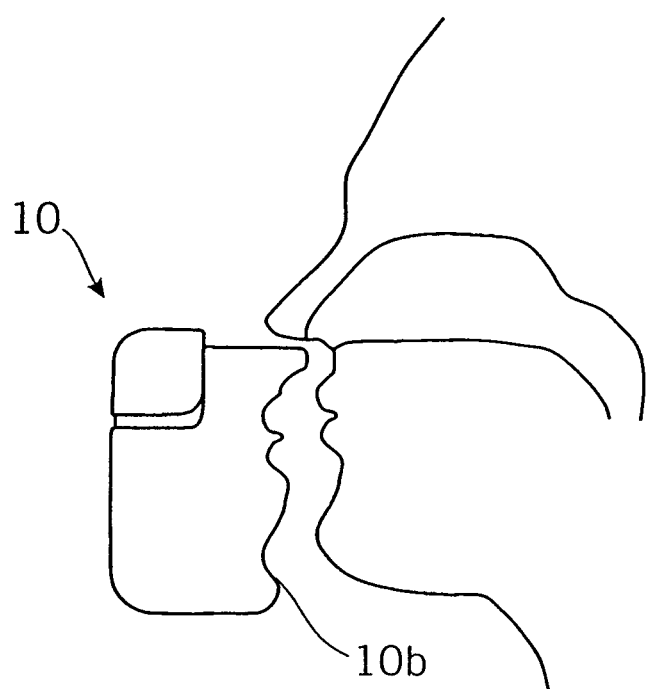
FIG. 6 shows an alternative embodiment of the discharge device.

FIGS. 1 and 2 show a side view and a front view of a discharge device according to the invention for nasal application of medicaments. FIG. 3 shows the discharge device in a perspective view. The discharge device 10 shown has a two-part housing 20 composed of interlocking housing halves 20a, 20b. Moreover, an actuating handle 30 is provided on a top face 10a of the housing 20 and can be moved in a vertical direction 2 relative to the housing 20.

On the right-hand side in FIG. 1, the housing is closed by a contact surface 10b, which is designed substantially flat in the sectional plane in FIG. 1. Between this contact surface 10b and the top face 10a, a nosepiece 70 is formed integrally in one piece onto the upper housing half 20a.

A pump dispenser 40, inserted into the housing 20, is composed of a pump arrangement 42 and of a media reservoir 44, on which the pump arrangement 42 is mounted. Between the actuating handle 30 and the pump arrangement 42 of the pump dispenser 40, there is an L-shaped channel section 50 by means of which a force applied to the actuating handle 30 in the vertical direction 2 is transmitted to the pump arrangement 42 and in this way permits actuation of the pump arrangement 42 by way of the actuating handle 30. The L-shaped channel section is mounted on the pump arrangement 42 in such a way that the medium delivered during a pumping operation is forced into the L-shaped channel section 50. The opposite end of the L-shaped channel section 50 is adjoined by a plastic tube 52, which is provided for conveying the medium to a discharge opening 72 at the distal end of the nosepiece 70.

The discharge device is configured as follows. The main body A comprises the greater part of the housing 20 and also the actuating handle 30. This main body A generally has a slim configuration extending in a principal direction of extent H1. The main body A is closed at its upper end by the top face 10a of the housing 10 and, on its right hand side in FIG. 1, which is directed toward the user during use, it is closed by the contact surface 10b. The contact surface 10b extends vertically along almost the complete length of the discharge device and is almost flat. As has already been described, the nosepiece 70 is arranged in a transition area between this contact surface 10b and the top face 10a. This nosepiece 70 is raised in relation to the contact surface 10b and thus protrudes beyond the plane formed by the contact surface 10b or beyond a plane aligned therewith, as shown by dots in FIG. 1. It thus extends in a principal direction of extent H2 which corresponds approximately to the direction of insertion of the nosepiece 70 and which corresponds through a connection line between a distal end 74 and the center point 76 of the cross-sectional surface in the plane of the contact surface 10b.

The actuation of the discharge device 10 by means of the actuating handle 30 takes place in the principal direction of extent H1. The principal direction of extent H1 of the main body A and the principal direction of extent H2 of the nosepiece 70 enclose an angle β of approximately 80°.

FIGS. 4a through 4c show the correct use of the discharge device.

Of these, FIG. 4a simply illustrates the orientation of the discharge device. As will be seen, the discharge device 10, in the orientation in which it is also shown in FIGS. 1 and 2, is brought close to the mouth and nose area of a patient 100 who is sitting upright or standing. Then, as is shown in FIG. 4b, a wing 102 of the user's nose is lifted slightly by means of the top face 10a. Thereafter, as is shown in FIG. 4c, the discharge device in its entirety is pressed closer to the user, whereupon the nosepiece 70 reaches the inlet area of the nasal cavity 104. In this state shown in FIG. 4c, the device is then actuated by pressing the actuating handle 30 down in the direction 2a. This leads to a spray 80, which reaches deep into the nasal cavity 104. Since the actuating direction 2a almost encloses a right angle with the principal direction of extent H2 of the nosepiece 70, the actuation does not usually cause a shifting of the nosepiece 70. There is therefore no risk of the user experiencing an unpleasant sensation caused by the nosepiece 70 being accidentally pushed in deeper or being pulled out during the course of the actuation.

The orientation of the nosepiece 70, together with the direction of spraying, which corresponds approximately to the principal direction of extent H2, results in particularly effective admission of the discharged medium 80 into the nasal cavity 104. The often incorrect use of nasal sprays, particularly involving discharging in the vertical direction, is avoided.

Incorrect use caused by tilting the discharge device 10 in the direction of the arrow 6 shown in FIG. 5a is not possible because the contact surface 10b of the discharge device 10 would then abut against the mouth or chin 106 of the user. However, there is also no risk of a complete pivoting that results in the discharge device being used as shown in FIG. 5b, since the slender shape of the discharge device 10 would make the position in FIG. 5b seem unusual to the user. Moreover, the actuating handle 30 would be difficult to operate in this position, and it would therefore be obvious that the type of use shown in FIG. 5b cannot be the intended one.

FIG. 6 shows an alternative design of a discharge device according to the invention. This second discharge device 10 corresponds in terms of its structure to the first embodiment described above, but it differs in that the contact surface has a configuration whose shape is adapted to the shape of the lip area and chin area of a user. The correct position of the discharge device during use is therefore made immediately apparent to the user.

The invention claimed is:

1. A discharge device in the form of a nasal spray for nasal application of medicaments by discharge of a spray jet, the discharge device comprising:
    a main body having a contact surface which, during use, is vertically oriented and is directed toward a face of a user;
    a nosepiece which is arranged in a fixed position with respect to the main body and is designed to be inserted into a nostril of the user, the nosepiece being provided on an upper edge area of the contact surface, protruding from the contact surface and having a discharge opening designed to discharge a spray jet;
    an actuating handle which is arranged on a top face of the main body and is moveable relative to the main body in an actuating direction, the actuating direction enclosing an angle of between 75° and 90° with a principal direction of extent of the nosepiece; and
    a pump device comprising a pump arrangement and an L-shaped channel mounted on the pump arrangement, an end of the L-shaped channel opposite the pump arrangement being joined to a flexible plastic tube for conveying the medicaments to the discharge opening.

2. The discharge device according to claim 1, wherein the contact surface has a height of at least 40 mm.

3. The discharge device according to claim 1, wherein the nosepiece protrudes from the contact surface by at least 10 mm.

4. The discharge device according to claim 1, wherein a principal direction of extent of the main body runs parallel to the contact surface.

5. The discharge device according to claim 1, wherein the principal direction of extent of the nosepiece encloses an angle of between 45° and 90° with a vertical direction.

6. The discharge device according to claim 1, wherein the nosepiece merges flush into a top face of the main body.

7. The discharge device according to claim 1, wherein the principal direction of extent of the nosepiece encloses an angle of between 0° and 30° with a discharge direction defined by a geometry of the discharge opening.

8. The discharge device according to claim 1, wherein the main body accommodates the pump arrangement whose pumping direction encloses an angle of between 0° and 10° with a vertical direction.

9. The discharge device according to claim 1, wherein the pump device is separate from and accommodated by the main body and comprises a media reservoir.

10. The discharge device according to claim 1, wherein the contact surface has a configuration whose shape is adapted to a shape of a lip area and/or a chin area of the user.

11. A discharge device for discharging fluid as a nasal spray for nasal application of medicaments as a spray jet, the discharge device comprising:

a main body having a contact surface which, during use, is vertically oriented and is directed toward a face of a user;

a nosepiece fixed to the main body and designed to be inserted into a nostril of the user, the nosepiece being located at an upper edge area of the contact surface, protruding from the contact surface and having a discharge opening forming a nozzle to discharge the fluid as the spray jet;

an actuating handle arranged on a top face of the main body and moveable relative to the main body in an actuating direction, the actuating direction enclosing an angle of between 75° and 90° with a principal direction of extent of the nosepiece; and a pump device located within the main body, the pump device comprising a pump and an L-shaped channel mounted on the pump, the L-shaped channel having a flexible plastic tube at an end of the L-shaped channel opposite the pump, the pump device conveying the medicaments to the discharge opening through the L-shaped channel and the flexible plastic tube.

12. The discharge device according to claim 11, wherein the nosepiece has a top surface, the top surface of the nosepiece being flush with the top face of the main body.

* * * * *